United States Patent [19]

Marschner et al.

[11] Patent Number: 5,410,027
[45] Date of Patent: Apr. 25, 1995

[54] METHOD OF PREPARING FIBER-REACTIVE FORMAZAN DYES INVOLVING HYDROLYSIS OF A FORMYL AMINO MOIETY

[75] Inventors: Claus Marschner, Speyer; Manfred Patsch, Wachenheim, both of Germany

[73] Assignee: BASF Aktiengesellschaft, Ludwigshafen, Germany

[21] Appl. No.: 74,608

[22] Filed: Jun. 11, 1993

[30] Foreign Application Priority Data

Jun. 13, 1992 [DE] Germany ............ 42 19 421.0

[51] Int. Cl.$^6$ ............ C09B 62/018; C09B 62/038; C09B 43/16; C09B 50/00
[52] U.S. Cl. ............ 534/598; 534/618; 534/652; 564/218; 564/223
[58] Field of Search ............ 534/618, 652, 598; 564/218, 223

[56] References Cited

U.S. PATENT DOCUMENTS

| | | | |
|---|---|---|---|
| 3,202,650 | 8/1965 | Steineman | 534/652 X |
| 3,627,749 | 12/1971 | Ackermann et al. | 534/652 X |
| 3,926,942 | 12/1975 | Yelland | 534/652 X |
| 4,720,542 | 1/1988 | Omura et al. | 534/618 |
| 4,906,736 | 3/1990 | Schwaiger et al. | 534/618 |
| 4,935,500 | 6/1990 | Omura et al. | 534/618 |
| 5,015,731 | 5/1991 | Schwaiger et al. | 534/618 |
| 5,107,022 | 4/1992 | De Besset | 564/223 |
| 5,145,483 | 9/1992 | Junino et al. | 564/223 X |

FOREIGN PATENT DOCUMENTS

| | | | |
|---|---|---|---|
| 0280139 | 8/1988 | European Pat. Off. | 534/618 |
| 0315046 | 5/1989 | European Pat. Off. | 534/618 |
| 3607825 | 9/1986 | Germany | 534/618 |
| 4142132 | 5/1993 | Germany | 564/218 |

*Primary Examiner*—Floyd D. Higel
*Attorney, Agent, or Firm*—Oblon, Spivak, McClelland, Maier & Neustadt

[57] ABSTRACT

Fiber-reactive formazan dyes are prepared by diazotizing a protectively formylated hydroxyphenylenediamine, coupling with a hydrazone compound, metallizing, eliminating the protective group, and reacting with a halotriazine and optionally thereafter with an amine or a hydroxy compound via novel aminophenol intermediates.

10 Claims, No Drawings

METHOD OF PREPARING FIBER-REACTIVE FORMAZAN DYES INVOLVING HYDROLYSIS OF A FORMYL AMINO MOIETY

BACKGROUND OF THE INVENTION

1. Field of the Invention

The present invention relates to a novel process for preparing fiber-reactive formazan dyes by diazotizing a protected hydroxyphenylenediamine compound, coupling with a hydrazone compound, metallizing, eliminating the protective group, and reacting with a halotriazine and optionally thereafter with an amine or a hydroxy compound. The present invention also relates to novel aminophenols.

2. Description of the Background

EP-A-280 139 discloses preparing aminoformazan dyes by reacting the arylhydrazone with a diazotized o-hydroxyaminobenzene. Amino groups to be present in the end product must be protectively acetylated before the reaction and the protective acetyl group must be reeliminated afterwards.

However, the alkaline hydrolysis of the protective group requires high alkali concentrations, high reaction temperatures and long reaction times.

A further disadvantage of existing processes is that, prior to the reaction with hydrolysis-sensitive fiber-reactive components, eg. with halotriazines, the alkaline solution must first be neutralized, which produces appreciable amounts of salt.

SUMMARY OF THE INVENTION

It is an object of the present invention to provide an economically and ecologically improved process for preparing aminoformazan compounds which avoids the problems mentioned and makes possible the synthesis of aminoformazan compounds and their further reaction to form reactive dyes in a high space-time yield.

DETAILED DESCRIPTION OF THE PREFERRED EMBODIMENTS

We have found that this object is achieved by a process for preparing fiber-reactive-formazan dyes which in the form of the free acid conform to the formula I where
cat$^\oplus$ is one equivalent of a cation,
n is 1 or 2,
X is oxygen or a radical of the formula CO—O or SO$_2$—O,
Me is copper or nickel,
Y is halogen,
Z for n=1 is halogen, C$_1$–C$_4$-alkoxy, amino, mono- or di(C$_1$–C$_4$-alkyl)amino, substituted C$_2$–C$_4$-alkylamino or phenyl- or N-(C$_1$–C$_4$)-N-phenylamino, wherein the phenyl group may in each case be substituted, or for n=2 is a radical of the formula where L is C$_2$–C$_6$-alkylene or unsubstituted or hydroxysulfonyl-substituted phenylene and Y is as defined above, and
the-rings A, B and C may carry further substituents,
which comprises a) as step 1 diazotizing an aminophenol of the formula II (II)

where the ring C is as defined above, coupling with a coupling component of the formula III (III)

where X and the rings A and B are each as defined above, and before, during or after the coupling reaction adding a copper or nickel salt, b) as step 2 hydrolyzing the resulting formazan compound of the formula IV (IV)

where cat$^\oplus$, X, Me and the rings A, B and C are each as defined above, under acid or base catalysis, and c) as step 3 reacting the resulting amino compound with a halotriazine of the formula Va or Vb

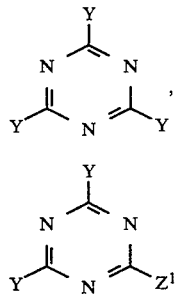

where Y is in either case as defined above and $Z^1$ is $C_1$–$C_4$-alkoxy, amino, mono- or di($C_1$–$C_4$-alkyl)amino, substituted $C_2$–$C_4$-alkylamino, phenyl- or N- ($C_1$–$C_4$-alkyl) -N-phenyl-amino, wherein the phenyl group may in either case be substituted, or a radical of the formula

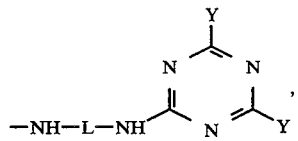

where L and Y are each as defined above.

cat$^\oplus$ is one equivalent of a cation. It is either a proton or derived from metal or ammonium ions. Metal ions are in particular the lithium, sodium or potassium ions. Ammonium ions for the purposes of the present invention are substituted or unsubstituted ammonium cations. Substituted ammonium cations are for example monoalkyl-, dialkyl-, trialkyl-, tetralkyl- or benzyltrialkyl-ammonium cations or those cations that are derived from nitrogen-containing five- or six-membered saturated heterocycles, such as pyrrolidinium, piperidinium, morpholinium, piperazinium or N-alkylpiperazinium cations or their N-monoalkyl- or N,N-dialkyl-substituted products. Alkyl is here to be understood as meaning in general straight-chain or branched $C_1$–$C_{20}$-alkyl, which may be substituted by hydroxyl groups and/or interrupted by oxygen atoms in ether function.

Particularly noteworthy cations are protons and lithium, sodium and potassium ions.

The rings A, B and/or C in the formula I may have as further substituents for-example halogen, in particular chlorine or bromine, or hydroxysulfonyl, and then generally have one or two such substituents.

A substituted phenylamino Z in the formula I may have as substituents for example hydroxysulfonyl, 2-sulfatoethylsulfonyl, 2-chloroethylsulfonyl, 3-(2-sulfatoethylsulfonyl)propanoylamino, 3-(2-chloroethylsulfonyl)propanoylamino, 4-(2-sulfatoethylsulfonyl)-butyrylamino or 4-(2-chloroethylsulfonyl)-butyrylamino. The phenyl ring is then generally mono-substituted or disubstituted.

A substituted $C_2$–$C_4$-alkylamino Z in the formula I may have as substituents for example hydroxysulfonyl, 2-sulfatoethylsulfonyl or 2-chloroethylsulfonyl.

Y and Z are each for example fluorine, chlorine or bromine.

Z may also be for example methoxy, ethoxy, propoxy, isopropoxy, butoxy, isobutoxy, sec-butoxy, mono- or dimethylamino, mono- or diethylamino, mono- or dipropylamino, mono- or diisopropylamino, mono- or dibutylamino, N-methyl-N-ethylamino, 2-hydroxysulfonylethylamino, 2-chloroethylsulfonylamino, phenylamino, 2-, 3- or 4-hydroxysulfonylphenylamino, 3- or 4-(2-sulfatoethylsulfonyl)-phenylamino, 3- or 4-( 2-chloroethylsulfonyl)-phenylamino, N-methyl- or N-ethyl-N-[4-(2-sulfatoethylsulfonyl)phenyl]amino, 3- or 4-[4-(2-sulfatoethylsulfonyl)butyrylamino]phenylamino or 3- or 4-[4-(2-chloroethylsulfonyl)butyrylamino]phenylamino.

L is for example $(CH_2)_2$, $(CH_2)_3$, $(CH_2)_4$, $(CH_2)_5$, $(CH_2)_6$, $CH(CH_3)CH_2$, $CH(CH_3)CH(CH_3)$, 1,2-, 1,3- or 1,4-phenylene or 4-hydroxysulfonyl-1,3-phenylene.

Suitable copper or nickel salts for addition in reaction step 1 are in general divalent salts, such as cupric sulfate, cuptic chloride, cupric acetate, nickel chloride, nickel sulfate or nickel-acetate.

The process of the invention is advantageously carried out by diazotizing the aminophenol II in step 1 in a conventional manner, for example in an aqueous medium, with sodium or potassium nitrite in the presence of a mineral acid, for example hydrochloric acid or sulfuric acid, at from 0° to 10° C., or in an organic solvent at from 0° to 10° C. with nitrous esters or glycols as diazotizing reagent. The resulting-diazonium salt is then added, usually as a solution or suspension, to the coupling component III in an aqueous medium. The coupling is in general carried out at from 10° to 25° C. and at pH 6–10. Before, during or after the coupling reaction the reaction mixture has additionally added to it a copper or nickel salt.

Following a subsequent stirring phase at from 10° to 25° C. for about 1–4 hours, the formation of the formazan IV is complete.

Per mole of aminophenol II the amounts used are in general from 1.0 to 1.1 mol of diazotizing reagent, from 0.9 to 1.1 mol of coupling component III and from 0.9 to 1.2 mol of copper or nickel salt.

The formazan IV can either be isolated (for example by salting out) or hydrolyzed directly in the reaction solution under acid or base catalysis.

An acid-catalyzed hydrolysis as step 2 is in general carried out at a pH of from 1 to 3, preferably from 1 to 2, and at from 40° to 80° C. in an aqueous medium. The acid used can be for example a mineral acid, such as hydrochloric acid, sulfuric acid or phosphoric acid. The amount of acid used per mole of formazan IV is in general about 2 mol equivalent.

A base-catalyzed hydrolysis is in general carried out in an aqueous medium at a pH of from 8 to 12, preferably from 10 to 11, and at from 40° to 80° C. The base used can be for example an aqueous solution (from 1 to 20% strength by weight ) of lithium, sodium or potassium hydroxide. The amount of base used per mole of formazan IV is in general from 3 to 12 mol equivalent.

Hydrolysis is complete after 0.5–2 h.

The subsequent step 3 comprises reacting the resulting amino compound of the formula IVa

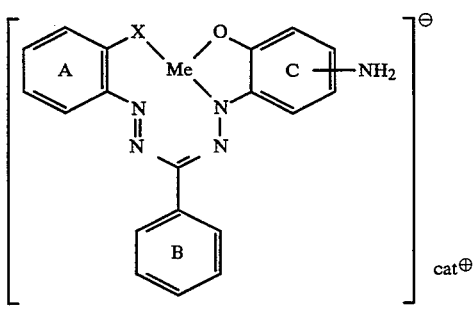

where cat⊕, X, Me and the rings A, B and C are each as defined above, with the triazine of the formula Va or Vb. For this the reaction solution is cooled down to room temperature and adjusted to a pH of 4–6. Then triazine Va or Vb is added. The pH of the reaction mixture is at the time maintained, for example with sodium bicarbonate, at from 4 to 4.5 and at from 0° to 25° C.

To prepare those compounds of the formula I where n is 2, the amino compound of the formula IVa is reacted with the triazine of the formula Vb where $Z^1$ is the abovementioned radical of the formula

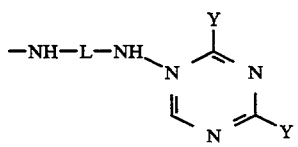

in a molar ratio of from 1.9:1 to 2.1:1.

When the reaction is carried out with the triazine of the formula Va, it is also possible to carry out a subsequent reaction with a compound of the formula VI $$Z^2\text{—H} \qquad\qquad (VI)$$

where $Z^2$ is $C_1$–$C_4$-alkoxy, amino, mono- or di($C_1$–$C_4$-alkyl)amino, substituted $C_2$–$C_4$-alkylamino or phenyl- or N-($C_1$–$C_4$-alkyl)-N-phenyl-amino, wherein the phenyl group may in either case be substituted. For this purpose the reaction mixture is admixed with from 1.0 to 1.2 mol of the compound VI, based on 1 mol of triazine Va, and subsequently stirred at from 40° to 60° C. and at a pH of 5.0 to 6.5, which may be set for example with sodium bicarbonate, for 1–8 hours.

After the reaction has ended, the dye can be isolated in a conventional manner, for example by spray drying or salting out.

Preference is given to employing the process for preparing formazan dyes of the formula I where two of the rings A, B and C are each monosubstituted by hydroxysulfonyl.

Preference is further given to employing the process for preparing formazan dyes of the formula I where Me is copper.

Preference is further given to employing the process for preparing formazan dyes of the formula I where Y is fluorine or chlorine, in particular chlorine.

The present invention further provides aminophenols of the formula II

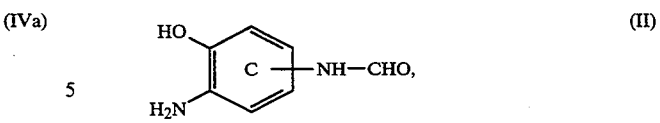

where the ring C can be substituted. Suitable substituents are for example those mentioned above by way of example.

As will be evident from the above observations, the aminophenols II are useful intermediates for the process of the invention.

They are prepared in a conventional manner. One method comprises for example formylating a nitrophenol of the formula IIa

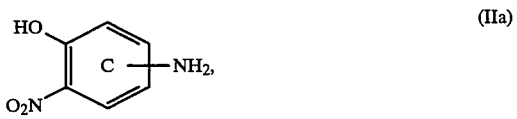

where the ring C is as defined above, with formic acid in an aqueous medium and then catalytically reducing the nitro group.

The amount of formic acid used in the formylation is in general from 1 to 15 mol per mole of nitrophenol IIa. The formylation itself is in general carried out at pH 1–5, preferably pH 2–3, and at from 30° to 80° C., preferably at from 35° to 50° C.

The other compounds employed in the process of the invention are known per se and described for example in the art cited at the beginning.

The advantage of the novel process is that the formazan dyes of the formula I can be prepared in a simple manner and in high purity and space-time yield. Compared with the hydrolysis of the protective acetyl group, which is very difficult to carry out, the formyl group can be eliminated under very mild conditions by both acid and alkaline hydrolysis.

The formazan dyes of the formula I are useful reactive dyes which are advantageous for dyeing or printing hydroxyl- or nitrogen-containing organic substrates. Such substrates include for example leather or fiber material that contains predominantly natural or synthetic polyamides or natural or regenerated cellulose. The dyes prepared by the novel process are preferable for dyeing and printing textile material based on cotton.

Embodiments of the invention will now be more particularly described by way of example.

EXAMPLE 1 a) 104.4 g of 2-formylamino-6-aminophenol-4-sulfonic acid were dissolved in 500 ml of water and adjusted with concentrated hydrochloric acid to a pH 2–2.3. Then 128 g of 23% strength by weight aqueous sodium nitrite solution were added at from 0° to 5° C. for diazotization. Thereafter excess nitrite was destroyed with 2 g of amidosulfuric acid.

The resulting diazonium suspension was added at from 10° to 15° C. to a mixture, adjusted to pH 6.5 to 7.0, of 144.0 g of hydrazone of the formula

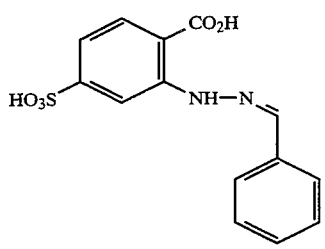

and 117.6 g of copper sulfate×5H$_2$O in 590 ml of water while the pH is maintained at from 6.5 to7.0. On completion of the addition the mixture was subsequently stirred at from 15° to 20° C. for 2 hours, at which point 300 g of sodium chloride were added. The salted-out product was filtered off and dried at 50° C. under reduced pressure, leaving 400 g of an electrolyte-containing compound of the formula

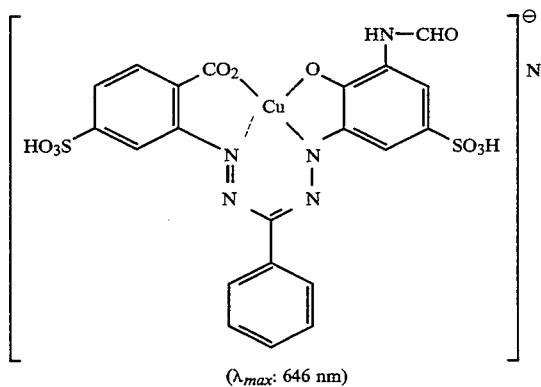

($\lambda_{max}$: 646 nm)

b1) 50 g of the compound obtained under a) were dissolved in 250 ml of water. The solution was adjusted to pH 1 with concentrated hydrochloric acid, then heated to 40°–45° C. and stirred at that temperature until elimination of the protective formyl group was complete (TLC), which took about 4 hours.

After cooling down to room temperature the reaction mixture was adjusted to pH 6.0–6.5 with sodium carbonate and the product was salted out with 100 g of sodium chloride. Drying left 61 g of the electrolyte-containing compound of the formula

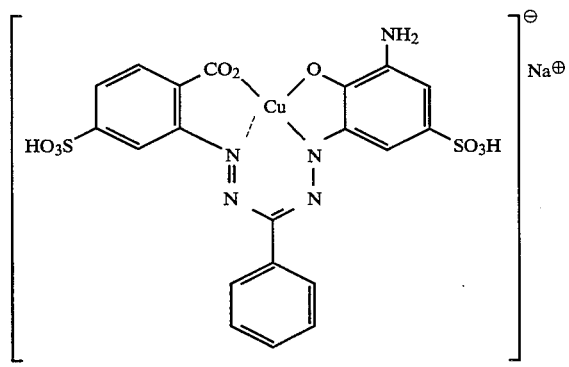

b2) 50 g of the compound obtained under a) were dissolved in 250 ml of 5% strength by weight sodium hydroxide solution and heated to 60° C. The mixture was subsequently stirred at that temperature for 30 minutes (average time TLC indicated complete elimination of the protective group). The reaction mixture was then cooled down to room temperature and brought to pH 6.0–6.5 with concentrated hydrochloric acid. Salting out, filtration and drying under reduced pressure at 50° C. left 63 g of the electrolyte-containing compound of the formula

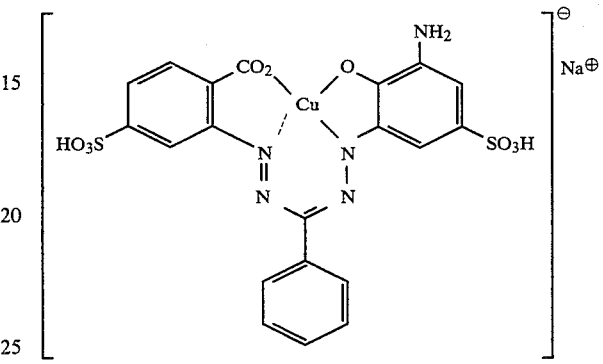

The same method gives the formazans listed below in Table 1.

TABLE 1

| Example No. | Copper formazan |
|---|---|
| 2 | 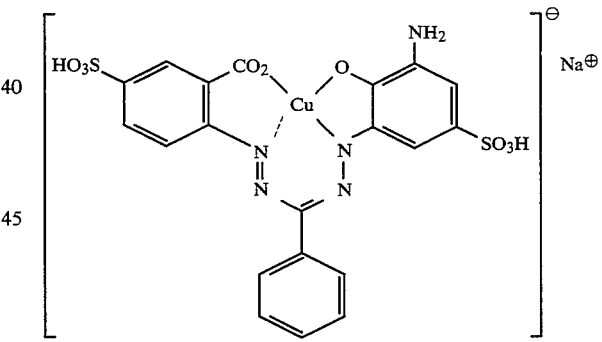 |
| 3 | 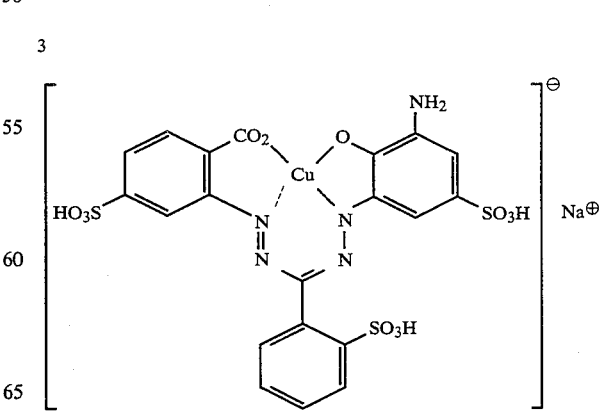 |
| 4 | |

TABLE 1-continued

| Example No. | Copper formazan |
|---|---|
| | 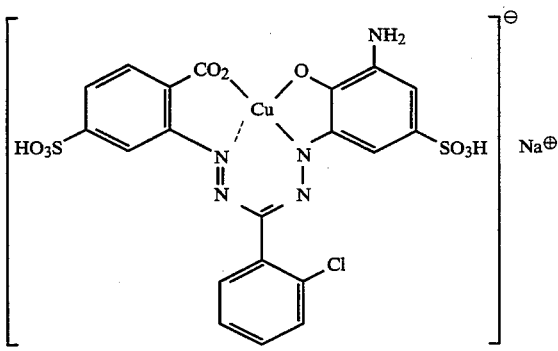 |
| 5 | |
| | 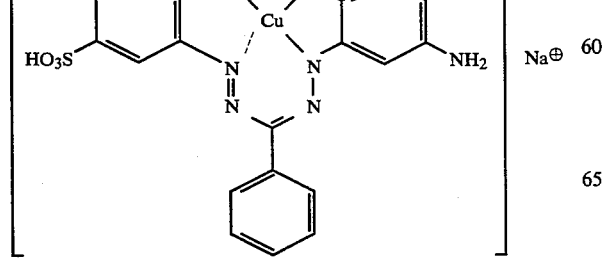 |
| 60 | |
| 65 | |

EXAMPLE 6

The reaction solution obtained in Example 1a) before salting out was brought to pH 1 with concentrated hydrochloric acid and then heated to 40°–45° C. It was subsequently stirred at that temperature for 4 hours, at which point the pH was raised to 4.0–4.5 with solid sodium carbonate.

After cooling down to room temperature, 83.0 g of cyanuric chloride were added. The pH of the reaction mixture was maintained at 4.0 to 4.5 with sodium bicarbonate until the acylation had ended. After 2 hours 80 g of 3-aminobenzenesulfonic acid, dissolved in 150 ml of water, were added. The suspension was heated to 40° to 45° C. and maintained at pH 6.0–6.5 with sodium bicarbonate.

After 6 hours the formazan dye of the formula

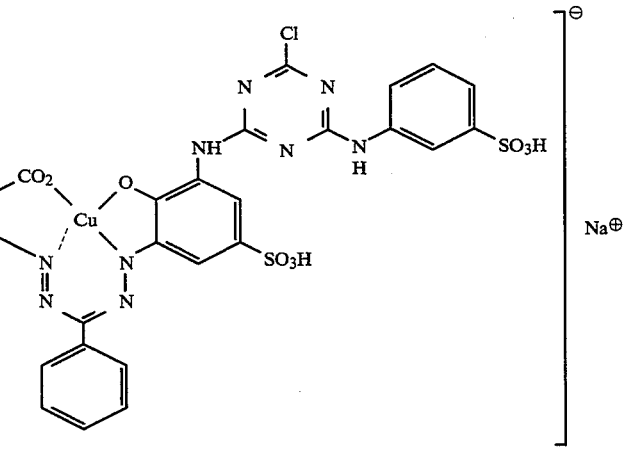

was isolated by salting out.

The same method gives the formazan dyes of the formula

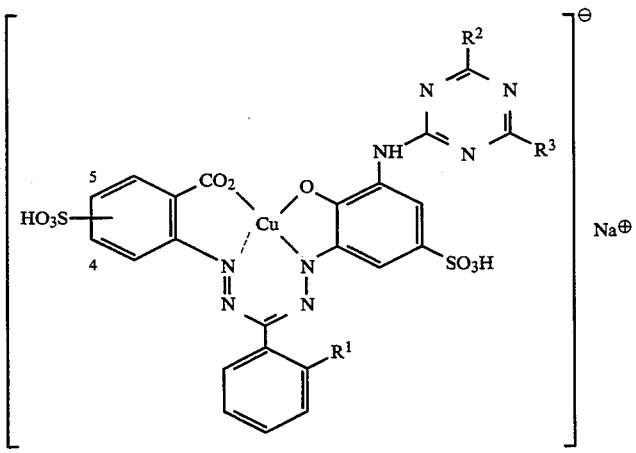

listed below in Table 2.

TABLE 2

| Ex. No. | Position of SO₃H group | R¹ | R² | R³ |
|---|---|---|---|---|
| 7 | 5 | H | F | 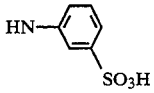 |
| 8 | 4 | H | Cl | 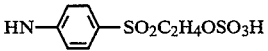 |
| 9 | 4 | H | Cl | 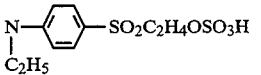 |

TABLE 2-continued

| Ex. No. | Position of SO₃H group | R¹ | R² | R³ |
|---|---|---|---|---|
| 10 | 4 | H | Cl |  |
| 11 | 4 | SO₃H | Cl | 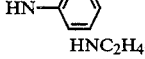 |
| 12 | 5 | H | F | HNC₂H₄SO₂C₂H₄Cl |
| 13 | 4 | SO₃H | Cl | HNC₂H₄SO₃H |

EXAMPLE 14

Example 6 was repeated replacing the 3-amino-benzenesulfonic acid by 45.5 g of 4-amino-2-methylamino-benzenesulfonic acid dissolved in 100 ml of water.

The suspension was heated to 60° C. and the pH was maintained at from 7.0 to 7.5 with sodium bicarbonate. After 6 hours the reaction mixture was spray dried to isolate the electrolyte-containing formazan dye which in the form of the free acid conforms to the following formula:

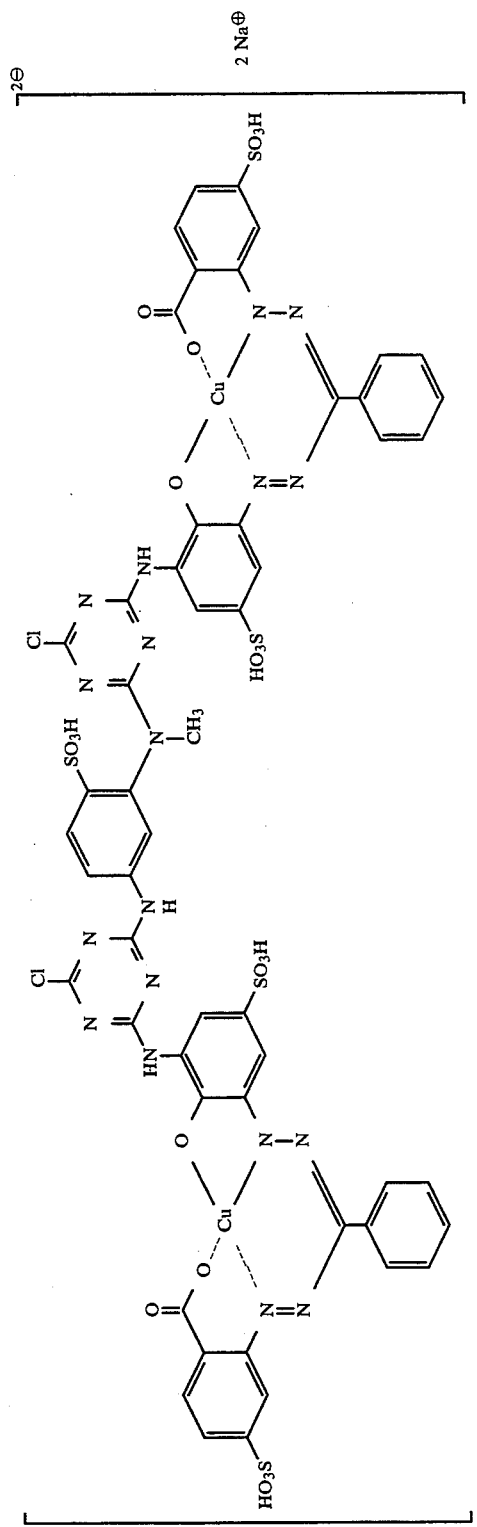

EXAMPLE 15 a) 233.5 g of 2-amino-6-nitrophenol-4-sulfonic acid were dissolved in 1 l of water at 60° C. The pH was set to 2 with sodium carbonate. Then 234.7 g of formic acid were added dropwise in the course of 30 minutes during which the pH was held at 2 with 50% strength by weight sodium hydroxide solution.

The reaction mixture was subsequently stirred at 60° C. for 4 hours. It was then cooled down to 0°–5° C. and adjusted to pH 6.8 with 50% strength by weight sodium hydroxide solution, and the precipitated product was filtered off with suction. Drying under reduced pressure at 60° C. left 466.8 g of the electrolyte-containing compound of the formula

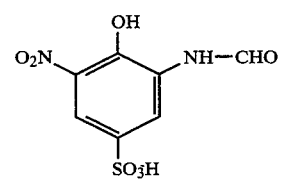

(Purity as per HPLC: 97%) $^1$H NMR [$d^6$-DMSO]: δ=7.9, 8.4 (aromatic H, CHO), 9.5 (NH) ppm.

b) 465 g of the formylated nitro compound obtained under a) were suspended in 1.4 l of water and, after 15 g of Raney nickel were added, hydrogenated with hydrogen (hydrogen pressure: 2 bar) at room temperature. After the absorption of hydrogen had ended, the catalyst was filtered off and the mother liquor was freed of solvent. This left 460 g of the electrolyte-containing compound of the formula

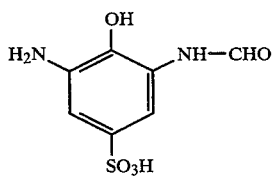

which can be used for dye syntheses without further purification.

We claim:

1. A process of preparing a fiber-reactive formazan dye which in the form of the free acid conforms to the formula (I):

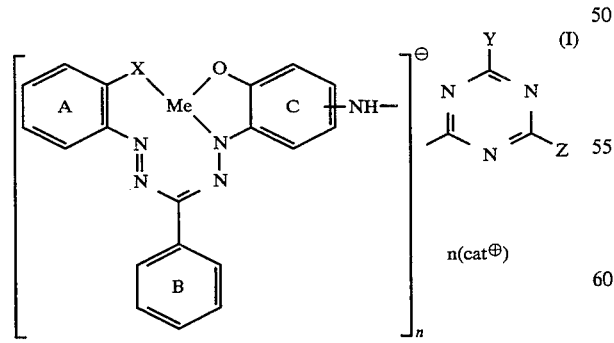

wherein
cat⊕ is one equivalent of a cation,
n is 1 or 2,
X is oxygen or a radical of the formula CO—O or SO$_2$—O,
Me is copper or nickel,
Y is halogen,
Z when n is 1, is halogen, C$_1$–C$_4$-alkoxy, amino, mono- or di-(C$_1$–C$_4$-alkyl)amino, substituted C$_2$–C$_4$-alkylamino substituted by hydroxysulfonyl, 2-sulfatoethylsulfonyl or 2-chloroethylsulfonyl; phenyl or N-(C$_1$–C$_4$-alkyl)-N-phenylamino, where each of said phenyl groups is unsubstituted or substituted by hydroxysulfonyl, 2-sulfatoethylsulfonyl, 2-chloroethylsulfonyl, 3-(2-sulfatoethylsulfonyl)-propanoylamino, 4-(2-sulfatoethylsulfonyl)-butyrylamino or 4-(2-chloroethylsulfonyl)-butyrylamino; or when n is 2, is a radical of the formula:

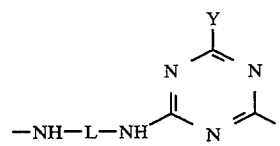

where L is C$_2$–C$_6$-alkylene or unsubstituted or hydroxysulfonyl-substituted phenylene and Y is as defined above, and the rings A, B and C are unsubstituted or substituted by one or two halogen or hydroxysulfonyl groups; which method comprises:

a) diazotizing an aminophenol of the formula (II):

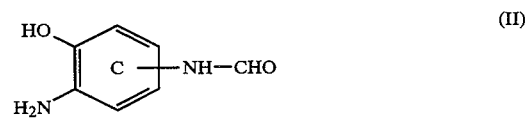

where the ring C is as defined above, coupling with a coupling component of the formula (III):

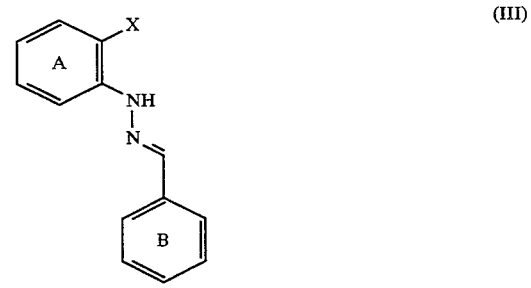

where X and the rings A and B are each as defined above, and before, during or after the coupling reaction reacting with a copper or nickel salt, b) hydrolyzing the resulting formazan compound of the formula (IV):

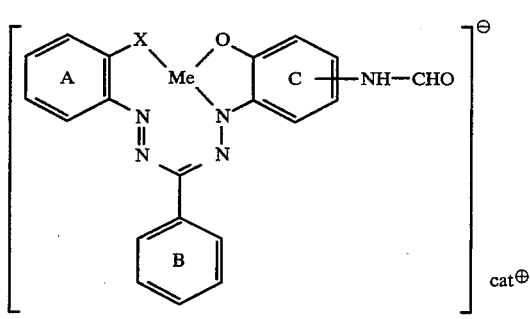

where cat⊕, X, Me and the rings A, B and C are each as defined above, under acid or base catalysis, and c) reacting the resulting amino compound with a triazine of the formula (Va) or (Vb):

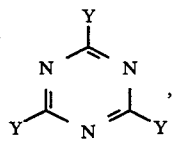

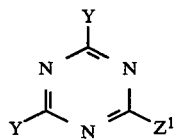

wherein Y is in either case as defined above, and $Z^1$ is $C_1$–$C_4$-alkoxy, amino, mono- or di-($C_1$ –$C_4$-alkyl)amino, substituted $C_2$–$C_4$-alkylamino, phenyl- or N-($C_1$–$C_4$-alkyl)-N-phenylamino, wherein each phenyl group is unsubstituted or substituted as defined above, or a radical of the formula:

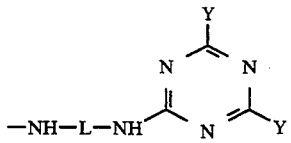

wherein L and Y are each as defined above.

2. The process as claimed in claim 1, wherein in formula (I), two of the rings A, B and C are each monosubstituted by hydroxysulfonyl.

3. The process as claimed in claim 1, wherein Me is copper.

4. The process as claimed in claim 1, wherein cat ⊕ is selected form the group consisting of hydrogen, lithium, sodium, potassium, unsubstituted ammonium, $C_1$–$C_{20}$ monoalkyl-, $C_1$–$C_{20}$-dialkyl, $C_1$–$C_{20}$-trialkyl, $C_1$–$C_{20}$-tetralkyl, benzyl-$C_1$–$C_{20}$-trialkyl-ammonium, pyrrolidinium, piperidinium, morpholinium, piperazinium, N-$C_1$–$C_{20}$-alkylipiperazinium; and pyrrolidinium, piperidinium, morpholinium, piperazinium, N-$C_1$–$C_{20}$-monoalkyl and N,N-$C_1$–$C_{20}$-dialkyl.

5. The process as claimed in claim 1, wherein L is selected from the group consisting of $-(CH_2)_2-$, $-(CH_2)_3-$, $-(CH_2)_4-$, $-(CH_2)_5-$, $-(CH_2)_6-$, $-(CH(CH_3)CH_2)-$, $-CH(CH_3)CH(CH_3)-$, 1,2-, 1,3-, 1,4-phenylene and 4-hydroxysulfonyl-1,3,-phenylene.

6. The process as claimed in claim 1, wherein said hydrolysis in step b) is effected at a pH of from 1 to 3 and at a temperature of from 40° to 80° C. in an aqueous medium.

7. The process as claimed in claim 1, wherein said hydrolysis in step b) is effected at a pH of from 8 to 12 and at a temperature of from 40° to 80° C. in an aqueous medium.

8. The process as claimed in claim 6, wherein said hydrolysis is complete after about 0.5 to 2 hours of hydrolysis.

9. The process as claimed in claim 7, wherein said hydrolysis is complete after about 0.5 to 2 hours of hydrolysis.

10. The process as claimed in claim 1, wherein Y is chlorine.

* * * * *